United States Patent [19]

Ogawa et al.

[11] Patent Number: 5,089,176

[45] Date of Patent: Feb. 18, 1992

[54] OPTICALLY ACTIVE MONOESTER COMPOUNDS AND PRODUCING

[75] Inventors: Tetsuya Ogawa, Futtsu; Naoyuki Yoshida, Ichihara; Seiichi Takano; Kunio Ogasawara, both of Sendai, all of Japan

[73] Assignee: Chisso Corporation, Osaka, Japan

[21] Appl. No.: 569,284

[22] Filed: Aug. 17, 1990

[30] Foreign Application Priority Data

Oct. 9, 1989 [JP] Japan .................................. 1-263409

[51] Int. Cl.$^5$ .......................... C09F 5/08; C09F 7/10
[52] U.S. Cl. .................................. 260/410; 435/134; 435/135; 435/824; 435/829; 435/830; 435/874; 435/912; 435/921; 435/931; 435/939
[58] Field of Search ............... 260/410; 435/134, 135, 435/824, 829, 830, 874, 912, 921, 931, 939

[56] References Cited

PUBLICATIONS

Van der Eycken et al., Chemical Abstracts, vol. 112, No. 1, Jan. 1, 1990, p. 758, Abstract No. 7720z.
Baratti et al., Chemical Abstracts, vol. 107, No. 25, Dec. 21, 1987, p. 628, Abstract No. 234757g.
Coliet et al., Chemical Abstracts, vol. 88, No. 15, Apr. 10, 1978, p. 476, Abstract No. 104187z.

Primary Examiner—Jose G. Dees
Assistant Examiner—Deborah D. Carr
Attorney, Agent, or Firm—Wenderoth, Lind & Ponack

[57] ABSTRACT

An optically active monoester of the formula of

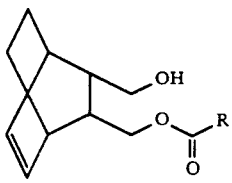

(I)

or

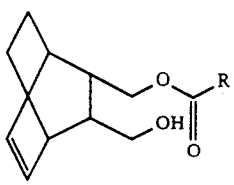

(I')

where R is $C_1$-$C_{15}$ alkyl is disclosed. The monoester is produced by transesterification of cis-endo-bicyclo [2,2,2] oct-5-ene-2,3-dimethanol with a fatty acid alkyl or vinyl ester, or triglyceride by using an esterase.

2 Claims, No Drawings

OPTICALLY ACTIVE MONOESTER COMPOUNDS AND PRODUCING

BACKGROUND OF THE INVENTION

1. Field of the Invention

The present invention relates to an optically active monoester compound of the formula (I) or (I'),

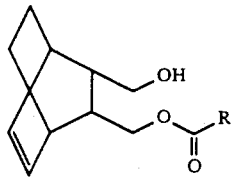
(I)

or

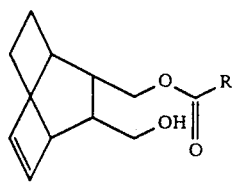
(I')

where R is an alkyl group of 1 to 15 carbon atoms and a process for producing said compound.

2. Description of Related Art

Syntheses of intermediates for pharmaceuticals and biologically active substances have recently increased. As a result, optically active starting materials for the syntheses of those materials are now in demand.

In particular, optically active analogues of bicyclo [2,2,2] oct-5-ene appear to be useful as starting materials for producing biologically active substances, but there are not so many compounds capable of being actually used therefor.

A compound of the formula,

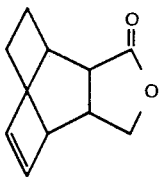
(III)

is known as a very useful compound as a starting material for biologically active substances such as a starting material for prostaglandin.

However, known processes for producing said compound are not practical. For example, J. B. Jones et al.: J. Am. Chem. Soc., Vol. 107, pp. 2521–6 (1985) discloses that the optically active lactone compound (III) above can be produced by converting a diol of the formula,

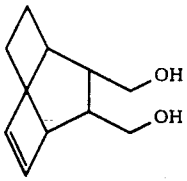
(II)

using a horse liver dehydrogenase.

However, this process has various drawbacks, e.g. the catalyst, horse liver dehydrogenase is expensive and, in addition, not easily available; a large amount of NAD (nicotinamide-adenine dinucleotide) is required; the reaction time is long (minimum 6 days) and the post-treatment is complicated (ether extraction for 12 hours).

In view of the foregoing, optically active analogues of bicyclo [2,2,2] oct-5-ene are in demand, but practically usable compounds have not yet been found. The present inventors did research and investigated these problems. They have now completed the present invention.

SUMMARY OF THE INVENTION

An object of the present invention is to provide a novel optically active bicyclo [2,2,2] oct-5-ene analogue. Another object of the present invention is to provide a process for producing said optically active bicyclo [2,2,2] oct-5-ene analogue.

According to one aspect, the present invention to provides an optically active cis-endo-2-acyloxymethyl-3-hydroxymethylbicyclo [2,2,2] oct-5-ene of the formula (I) or (I')

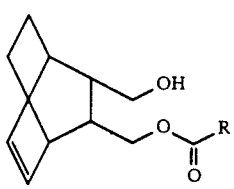
(I)

or

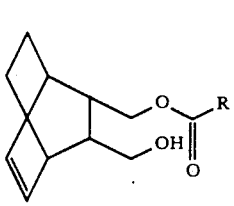
(I')

where R is an alkyl group of 1 to 15 carbon atoms.

According to another aspect, the present invention provides a process for producing an optically active cis-endo-2-acyloxymethyl-3-hydroxymethylbicyclo [2,2,2] oct-5-ene of the formula (I) or (I'),

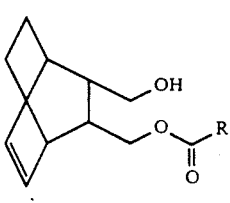
(I)

or

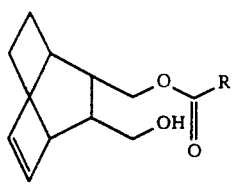
(I')

where R is an alkyl group of 1 to 15 carbon atoms which comprises a transesterification reaction between cis-endo-bicyclo [2,2,2] oct-5-ene-2,3-dimethanol of the formula (II),

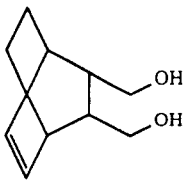
(II)

and a fatty acid alkyl ester, fatty acid vinyl ester or triglyceride by using an esterase.

DESCRIPTION OF THE PREFERRED EMBODIMENTS

Exemplary suitable optically active monoester compounds of the formula (I) or (I') above of the present invention include optically active cis-endo-2-acetyloxymethyl-3-hydroxymethylbicyclo [2,2,2] oct-5-ene, optically active cis-endo-2-propanoyloxymethyl-3-hydroxymethylbicyclo [2,2,2] oct-5-ene, optically active cis-endo-2-butanoyloxymethyl-3-hydroxymethylbicyclo [2,2,2] oct-5-ene, optically active cis-endo-2-pentanoyloxymethyl-3-hydroxymethylbicyclo [2,2,2] oct-5-ene, optically active cis-endo-2-hexanoyloxymethyl-3-hydroxymethylbicyclo [2,2,2] oct-5-ene, optically active cis-endo-2-decanoyloxymethyl-3-hydroxymethylbicyclo [2,2,2] oct-5-ene, and optically active cis-endo-2-undecanoyloxymethyl-3-hydroxymethylbicyclo [2,2,2] oct-5-ene.

The process for producing an optically active monoester compound may be represented by the following reaction schemes:

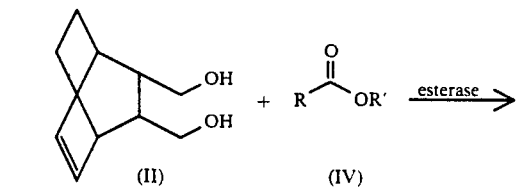

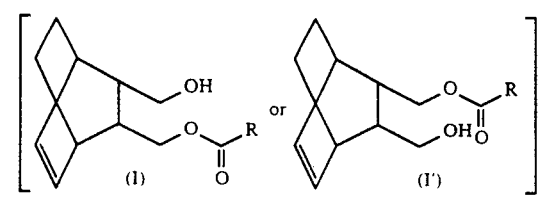

or $$R'OH + H_3C\overset{\underset{\|}{O}}{C}H$$

or (II) + (V) → esterase →

[ (I) or (I') ] +

$$\begin{matrix} -OH \\ -O\overset{\underset{\|}{O}}{C}R \\ -O\overset{\underset{\|}{O}}{C}R \end{matrix}$$

where R is an alkyl group of 1 to 15 carbon atoms and R' is alkyl or vinyl.

The reaction may be carried out by mixing cis-endo-bicyclo [2,2,2] oct-5-ene-2,3-dimethanol (II) and a fatty acid alkyl ester or fatty acid vinyl ester (IV), or triglyceride (V) with esterase in a solution so as to efficiently bring the compounds into contact with esterase, and as a result, an optically active monoester, i.e. optically active cis-endo-2-acyloxymethyl-3-hydroxymethylbicyclo [2,2,2] oct-5-ene (I) or (I'), is obtained.

As reaction conditions of the process of the present invention, the reaction temperature is appropriately about 10° C. to 150° C., preferably 20° C. to 45° C. and the reaction time varies depending upon the type of ester of the formula (IV) or (V), but is usually 1–1000 hours.

The starting material in the process for the production, cis-endo-bicyclo [2,2,2] oct-5-ene-2,3-dimethanol (II), may be easily obtained by reducing commercially available cis-endo-bicyclo [2,2,2] oct-5-ene-2,3-dicarboxylic acid anhydride with lithium aluminum hydride.

Esterases used in the present invention include esterases produced by microorganism and those derived from animals. Commercially available esterases are exemplified as shown in the following table.

TABLE

| Trade name | Origin | Seller or Maker |
|---|---|---|
| Lipase P | Pseudomonas fluorescens | Amano Pharmaceutical Co., Ltd |
| Lipase CES | Pseudomonas sp | Amano Pharmaceutical Co., Ltd |
| Lipase II | Porcine Pancreas | Sigma Chemical Co. |

| Trade name | Origin | Seller or Maker |
| --- | --- | --- |
| Lipase VIII | *Geotrichum Candidum* | Sigma Chemical Co. |
| Lipase X | *Rhizopus delamar* | Sigma Chemical Co. |
| Lipase AP | *Aspergillus niger* | Amano Pharmaceutical Co., Ltd |
| Lipase M | *Mucor javanicus* | Amano Pharmaceutical Co., Ltd |
| Lipase CE | *Humicola lanuginosa* | Amano Pharmaceutical Co., Ltd |
| Lipase F-AP | *Rhizopus javanicus* | Amano Pharmaceutical Co., Ltd |
| Lipase | *Chromobacterium Viscosum* | Toyo Jozo Co., Ltd. |
| Lipase A | *Aspergillus niger* | Novo Industi A/S |
| Lipase | *Rhizopus niveus* | Nagase Biochemicals, Ltd. |
| Lipase B | *Pseudomonas fragi* | Sapporo Beer Co. |

Other than above, any esterase derived from microorganisms capable of producing esterase may be used regardless of type of the esterase.

Examples of such microorganisms include the following genuses:
Pseudomonas,
Arthrobacter,
Acromobacter,
Alcaligenes,
Aspergillus,
Chromobacterium,
Candida,
Mucor, and
Rhizopus.

Among them, esterase derived from Pseudomonas genus is particularly preferable.

According to the process of the present invention, exemplary suitable fatty acid alkyl esters include methyl acetate, methyl propionate, ethyl acetate, methyl propionate, ethyl propionate, methyl caproate, ethyl caproate, propyl acetate and butyl acetate; exemplary suitable fatty acid vinyl esters include vinyl acetate, vinyl propionate, vinyl caproate, and vinyl laurate; and exemplary suitable triglycerides include triacetin, tripropionin, tributyrin, and tricaproin. A fatty acid alkyl ester or vinyl ester, or triglyceride is usually used in an amount ranging from a large excess as compared with cis-endo-bicyclo [2,2,2] oct-5-ene-2,3-dimethanol (II) to a molar ratio of the ester or triglyceride to the bicyclo compound (II) being 1:1. Preferable amounts thereof are such that both compounds can be mixed to form a uniform system.

In the process of the production of the present invention, after completion of the transesterification, the esterase powder is removed by an ordinary filtration procedure and the esterase thus recovered can be used again as it is.

The resulting optically active monoester, i.e. optically active cis-endo-2-acyloxymethyl-3-hydroxymethylbicyclo [2,2,2] oct-5-ene can be isolated by subjecting the filtrate, i.e. the liquid reaction mass to a distillation under reduced pressure or column chromatography.

The optically active cis-endo-2-acyloxymethyl-3-hydroxymethylbicyclo [2,2,2] oct-5-ene of the present invention has been produced for the first time by the present inventors and is a novel compound. It is useful as an intermediate for producing pharmaceuticals.

For example, after protecting the hydroxyl group of said bicyclo compound with an appropriate protecting group such as tetrahydropyranyl group, the thus protected bicyclo compound is subjected to ester hydrolysis, oxidation and deprotection resulting in forming the compound of the formula (III),

In addition, the compound of the present invention is very useful as a chiral synthon. That is, it can be a starting material for producing prostaglandin, alkaloids and the like which are biologically active natural products.

The production process of the present invention has the following advantages.

(i) Optically active cis-endo-2-acyloxymethyl-3-hydroxymethylbicyclo [2,2,2] oct-5-ene can be very rapidly produced by a one-step reaction.

(ii) Since the reaction is effected under the condition that water is not substantially present, a side reaction, i.e. hydrolysis, hardly occurs.

(iii) The reaction proceeds at a relatively low temperature and therefore, any particular equipment is not required.

(iv) The used esterase can be easily recovered and used again.

(v) Since neither buffer solution nor solvent is necessary, the concentration of the substrate can be made high so that a large volume of a reaction vessel is not necessary.

The following examples are given by way of illustration and not limitation of the present invention.

EXAMPLE 1

In a 100 ml. round bottom flask, 0.97 g (10 m mol) of cis-endo-bicyclo [2,2,2] oct-5-ene-2,3-dimethanol (II) was dissolved in 35 ml. of vinyl acetate at room temperature and 3 g. of Lipase P (manufactured by Amano Pharmaceutical Co., Ltd.) was added thereto followed by stirring at room temperature for 15 hours.

The reaction was confirmed by using gas chromatography. Then, the Lipase P was filtered and vinyl acetate was distilled off under reduced pressure to obtain 2.08 g. of a residue.

The resulting optically active cis-endo-2-acetyloxymethyl-3-hydroxymethylbicyclo [2,2,2] oct-5-ene was isolated from the residue by a silica gel column chromatography (toluene:ethyl acetate=1:1), and recrystallized from n-heptane to obtain 0.80 g. (3.37 m mol) of optically active cis-endo-2-acetyloxymethyl-3-hydroxymethylbicyclo [2,2,2] oct-5-ene.

Specific rotation of this compound was

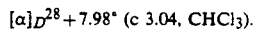

EXAMPLE 2

In a 100 ml. round bottom flask, 1.68 g. (10 m mol) of cis-endo-bicyclo [2,2,2] oct-5-ene-2,3-dimethanol (II) was dissolved in 60 ml. of ethyl acetate, and 5 g. of Lipase II (manufactured by Sigma Chemical Co.) was added thereto followed by stirring at room temperature for 48 hours.

The reaction was confirmed by using gas chromatography. Then, Lipase II was filtered off and ethyl acetate was distilled off under reduced pressure to obtain 2.06 g. of residue, from which optically active cis-endo-2-acetyloxymethyl-3-hydroxymethylbicyclo [2,2,2] oct-5-ene was separated by means of silica gel column chromatography (toluene:ethyl acetate=1:1).

The optically active bicyclo compound thus separated was recrystallized from n-heptane to obtain 0.60 g (3.01 m mol) of optically active cis-endo-2-acetyloxymethyl-3-hydroxymethylbicyclo [2,2,2] oct-5-ene, which had a specific rotation of $[\alpha]_D^{30} + 5.38°$ (c 1.087, CHCl$_3$).

EXAMPLE 3

In a 100 ml. round bottom flask, 1.68 g. (10 m mol) of cis-endo-bicyclo [2,2,2] oct-5-ene-2,3-dimethanol (II) was dissolved in 60 ml. of vinyl acetate at room temperature and 5 g. of Lipase II (Sigma Chemical Co.) was added thereto followed by stirring at room temperature for 48 hours.

The reaction was confirmed by using gas chromatography. The Lipase II was then filtered off and vinyl acetate distilled off under reduced pressure to give 2.08 g. of residue. The residue was treated by silica gel column chromatography (toluene:ethyl acetate =1:1) to separate the resulting(optically active cis-endo-bicyclo [2,2,2] oct-5-ene-2-acetyloxymethyl-3-hydroxymethyl.

The optically active bicyclo compound thus separated was recrystallized from n-heptane to obtain 1.26 g. (5.88 m mol) of optically active cis-endo-2-acetyloxymethyl-3-hydroxymethyl-bicyclo [2,2,2] oct-5-ene, which had a specific rotation of $[\alpha]_D^{28} + 7.10°$ (c 1.03, CHCl$_3$).

What is claimed is:

1. An optically active cis-endo-2-acyloxymethyl-3-hydroxymethylbicyclo [2,2,2] oct-5-ene of the formula (I) or (I')

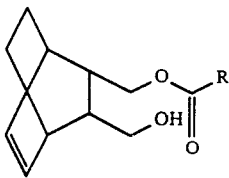
(I)

or

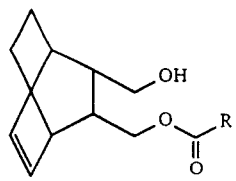

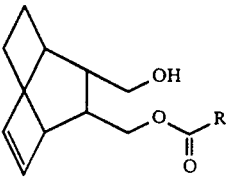
(I')

where R is an alkyl group of 1 to 15 carbon atoms.

2. A process for producing an optically active cis-endo-2-acyloxymethyl-3-hydroxymethylbicyclo [2,2,2] oct-5-ene of the formula (I) or (I'),

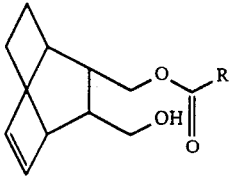
(I)

or (I')

where R is an alkyl group of 1 to 15 carbon atoms which comprises transesterifying cis-endo-bicyclo [2,2,2] oct-5-ene-2,3-dimethanol of the formula (II),

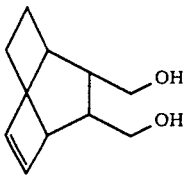
(II)

with a fatty acid alkyl ester, fatty acid vinyl ester or triglyceride by using an esterase derived from the genus Pseudonomas, Arthrobacter, Acromobacter, Alcaligenes, Aspergillus, Chromobacterium, Candida, Mucor, Rhizopus or Porcine Pancrease.

* * * * *